US012734310B2

(12) United States Patent
Carlsson

(10) Patent No.: US 12,734,310 B2
(45) Date of Patent: Sep. 15, 2026

(54) ACTIVATION ASSISTING ASSEMBLY FOR A MEDICAMENT DELIVERY DEVICE

(71) Applicant: SHL MEDICAL AG, Zug (CH)

(72) Inventor: Daniel Carlsson, Enskede (SE)

(73) Assignee: SHL Medical AG, Zug (CH)

( * ) Notice: Subject to any disclaimer, the term of this patent is extended or adjusted under 35 U.S.C. 154(b) by 610 days.

(21) Appl. No.: 18/038,801

(22) PCT Filed: Dec. 3, 2021

(86) PCT No.: PCT/EP2021/084084

§ 371 (c)(1), (2) Date: May 25, 2023

(87) PCT Pub. No.: WO2022/128522

PCT Pub. Date: Jun. 23, 2022

(65) Prior Publication Data

US 2024/0001045 A1 Jan. 4, 2024

(30) Foreign Application Priority Data

Dec. 17, 2020 (EP) .................................... 20215104

(51) Int. Cl.
*A61M 5/36* (2006.01)
*A61M 5/315* (2006.01)

(52) U.S. Cl.
CPC ............ *A61M 5/36* (2013.01); *A61M 5/3158* (2013.01)

(58) Field of Classification Search
CPC .. A61M 5/3158; A61M 5/20; A61M 5/31578; A61M 5/31566; A61M 2005/2006; A61M 2005/2073; A61M 5/31585
See application file for complete search history.

(56) References Cited

U.S. PATENT DOCUMENTS 3,565,070 A 2/1971 Hanson et al.
2002/0177808 A1 11/2002 Carmel
2009/0005735 A1 1/2009 Wikner et al.
2010/0010454 A1* 1/2010 Marshall ............. A61M 5/3202 604/208

FOREIGN PATENT DOCUMENTS

WO 2007/099044 A1 9/2007

OTHER PUBLICATIONS

International Search Report and Written Opinion for Int. App. No. PCT/EP2021/084084, mailed Jan. 4, 2022.

* cited by examiner

*Primary Examiner* — Nilay J Shah
(74) *Attorney, Agent, or Firm* — McDonnell Boehnen Hulbert & Berghoff LLP

(57) ABSTRACT

An activation assisting assembly for a medicament delivery device is provided where a first part has a first tubular portion extending along a longitudinal axis (L); wherein the first tubular portion comprises a cavity extending along the longitudinal axis (L) between a first end and a second end; wherein the second end of the cavity has an opening; a second part having a second tubular portion axially aligned with the first tubular portion, and being axially movable relative to the first tubular portion; wherein the second tubular portion has a recess facing towards the opening of the cavity of the first tubular portion; a pin movably connected to the second tubular portion; wherein the pin has an elongated body extending between a first end, distal from the recess of the second tubular portion, and a second end.

19 Claims, 4 Drawing Sheets

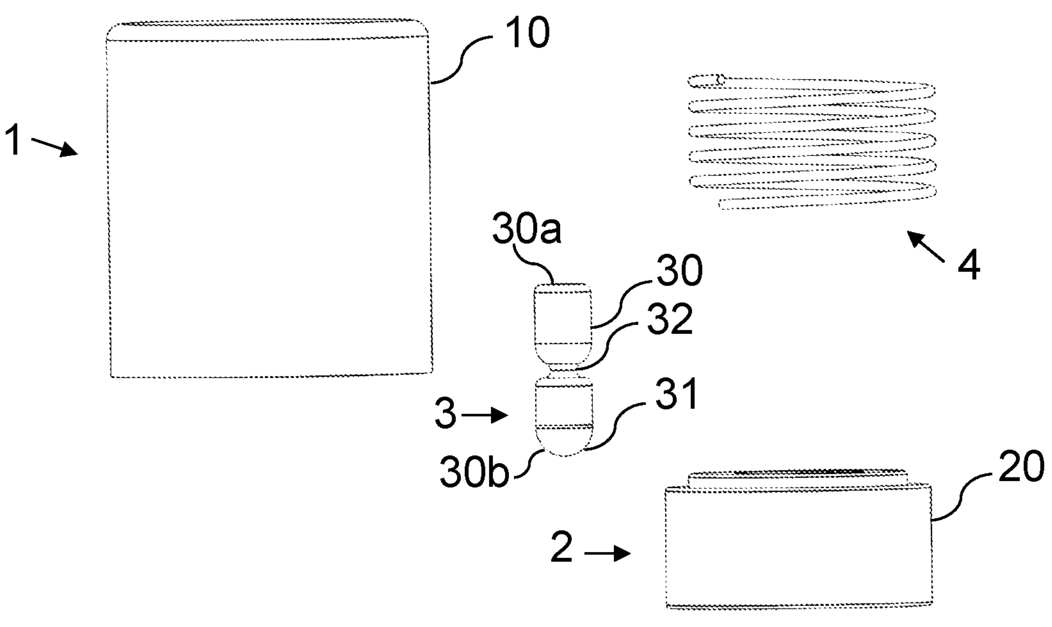
Fig. 1
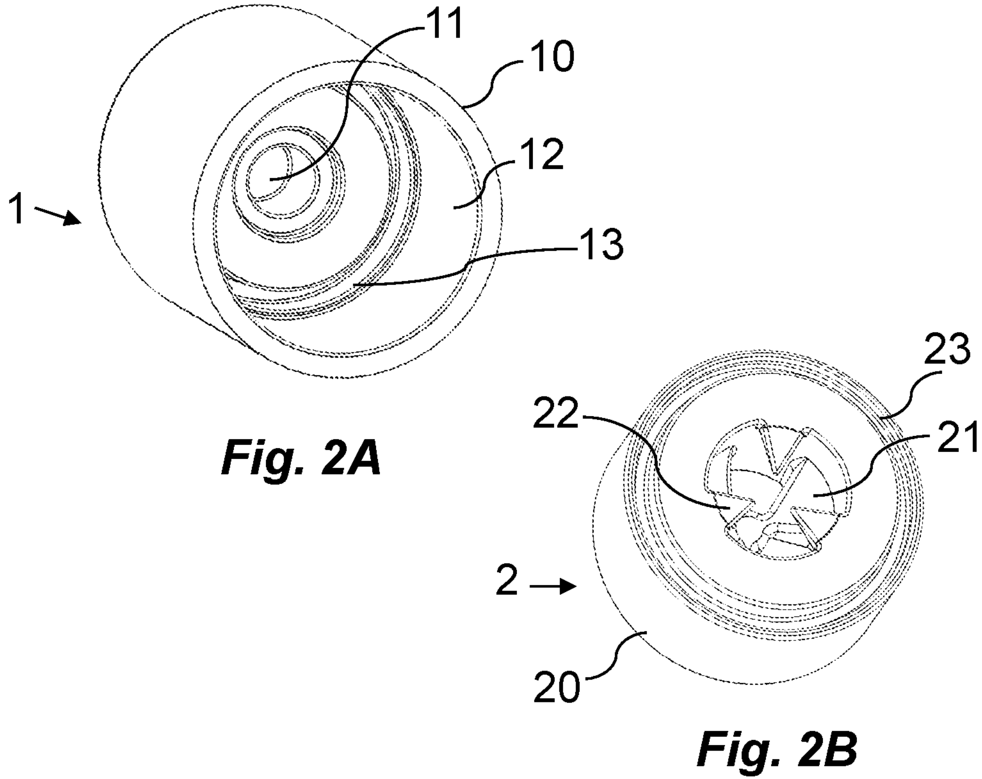
Fig. 2A
Fig. 2B

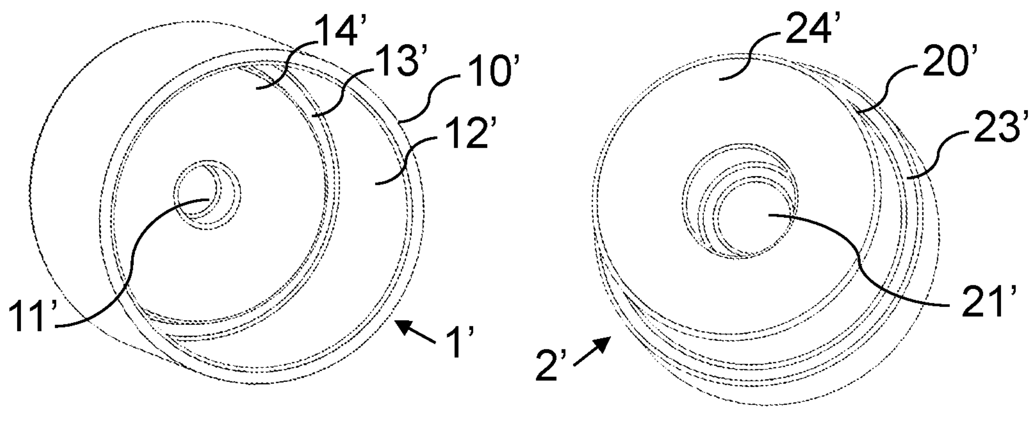
Fig. 5A
Fig. 5B
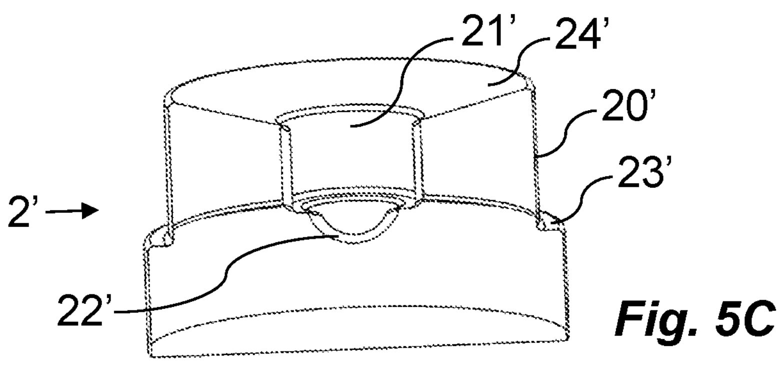
Fig. 5C
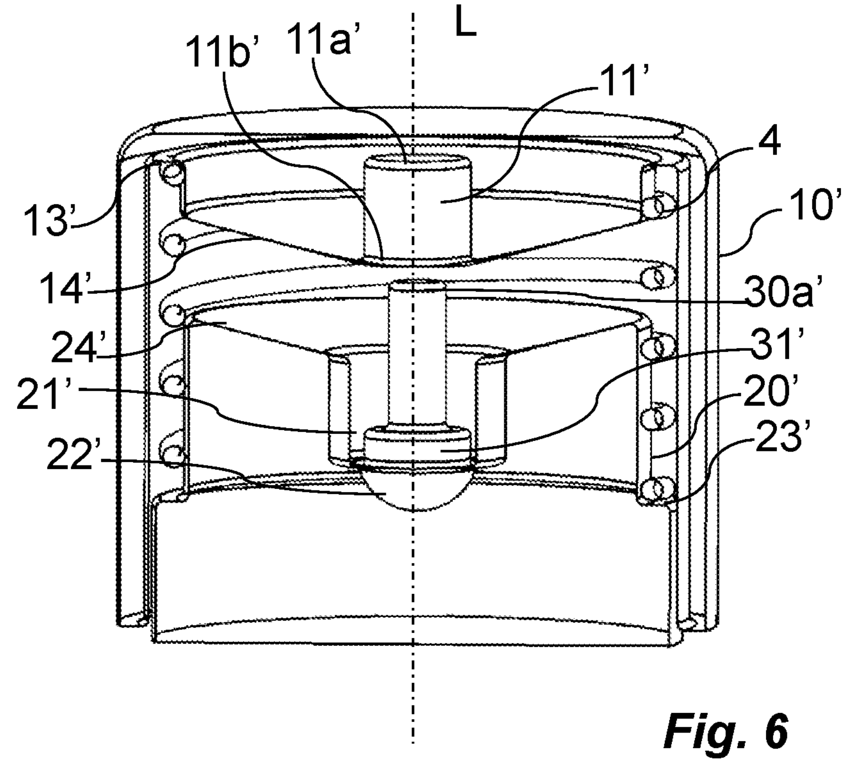
Fig. 6

ACTIVATION ASSISTING ASSEMBLY FOR A MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2021/084084 filed Dec. 3, 2021, which claims priority to European Patent Application No. 20215104.9 filed Dec. 17, 2020. The entire disclosure contents of these applications are herewith incorporated by reference into the present application.

TECHNICAL FIELD

The present disclosure generally relates to activation assisting assemblies for a medicament delivery device and particularly to an activation assisting assemblies with a pin.

BACKGROUND

Medicament delivery devices such as pen type injectors or safety syringes are generally known for the self-administration of a medicament by patients without formal medical training. As an example, those patients suffering from diabetes may require repeated injections of insulin; or other patients may require regular injections of other types of medicaments, such as a growth hormone.

Usually, a medicament delivery device comprises a medicament container, e.g. a syringe or a cartridge, and a medicament delivery member, e.g. a needle or a nozzle.

Some instructions for the use of medicament delivery devices instruct the user to hold the medicament delivery device with a certain orientation relative to a medicament delivery site or relative to the ground for performing an operation of the medicament delivery device. The reason for having such instructions may be because the medicament container contains some air. The air content may be unintentionally caused during the filling of containers, and some medicaments are also prone to creating bubbles. On the other hand, for preserving the medicament, the container may be intentionally filled with some air, for maintaining a sterilization of the container or for preventing the medicament from being oxidized.

If the contained air is delivered into the user's body, it may cause pain or even tissue damage. To prevent the air from being delivered into the user's body, some medicament delivery devices are designed with a priming function, meaning that the contained air will be expelled first, after which the user is able to perform the medicament delivery operation. In this scenario, the user needs to orient the medicament delivery device with a front end of the medicament delivery device pointing up, so that the air can accumulate at the front end and be removed during priming.

Alternatively, if the medicament delivery device has been held vertically, with a front end of the medicament container aiming towards the ground, the contained air will move to a back end of the medicament container due to the density difference; so that the user is able to expel the medicament into a medicament delivery site (that is be parallel to the ground), but leave the contained air in the medicament container.

In another example, some medicament delivery device operations, like injection, will require the user to hold the device at a certain angle relative to the medicament delivery site. For example, subcutaneous injections can be given straight in at a 90-degree angle or at a 45-degree angle, which varies the depth of needle penetration. For example, with 5 centimeters of needle, the injection should be given at a 90-degree angle if the injection site is around 5 centimeters depth from the skin surface; or at a 45-degree angle if the injection site is around 3.5 centimeters depth from the skin surface, so that the injection needle can reach to the correct depth for subcutaneous injections.

However, for operating a self-administration medicament delivery device, the user will not always read and/or follow the user guidance carefully; or sometimes the user may not pay much attention when operating the medicament delivery device especially if the user already done the repeating medicament delivery many times.

An incorrect orientation of the medicament delivery device during performing an operation of the medicament delivery device may cause such operation of the medicament delivery device to be less efficient or more uncomfortable for the user. Considering this, it has been appreciated that improvements can be made.

SUMMARY

The present disclosure is defined by the appended claims, to which reference should now be made.

In the present disclosure, when the term "back direction" is used, this refers to the direction pointing away from the dose delivery site during use of the medicament delivery device. When the term "back part/end" is used, this refers to the part/end of the delivery device, or the parts/ends of the members thereof, which under use of the medicament delivery device is/are located furthest away from the dose delivery site. Correspondingly, when the term "front direction" is used, this refers to the direction pointing towards the dose delivery site during use of the medicament delivery device. When the term "front part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the front end to the back end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", "circumferentially", "radial", "radially", "rotation", "rotational" and "rotationally" refer to a direction generally perpendicular to the longitudinal direction and at least partially extending around the longitudinal direction.

There is hence provided an activation assisting assembly for a medicament delivery device, the activation assisting assembly comprising: a first part having a first tubular portion extending along a longitudinal axis; the first tubular portion comprises a cavity extending along the longitudinal axis between a first end and a second end; the second end of the cavity comprises an opening; a second part having a second tubular portion axially aligned with the first tubular portion, and being axially movable relative to the first tubular portion; the second tubular portion comprises a recess facing towards the opening of the cavity of the first tubular portion; a pin movably connected to the second tubular portion; the pin comprises an elongated body extending between a first end, distal from the recess of the second tubular portion, and a second end proximal to the recess of the second tubular portion; the first end of the elongated body of the pin is dimensioned to fit into the cavity; the pin comprises a gravity portion where a center of gravity of the pin is located; the gravity portion is located closer to the second end of the elongated body of the pin than to the first end of the elongated body of the pin; the second end of the elongated body of the pin is arranged within the recess of the second tubular portion.

The activation assisting assembly can therefore help the user to hold the medicament delivery device with a predetermined orientation relative to the ground during performance of an operation of the medicament delivery device. With this structure, an activation mechanism of the medicament delivery device can be arranged to only be activated when the user holds the medicament delivery device with the predetermined orientation relative to the ground in a medicament delivery device comprising the activation assisting assembly.

According to another embodiment, the second end of the elongated body of the pin comprises a hemispherical or spherical surface.

According to another embodiment, the gravity portion of the pin comprises a material different from a material that the rest of the elongated body of the pin is made from.

According to another embodiment, a density of the material of the gravity portion of the pin is different from a density of the material that the rest of the elongated body of the pin is made from. Preferably, the density of the material of second end of the elongated body of the pin is higher than a density of the material that the rest of the elongated body of the pin is made from. According to another embodiment, the recess of the second tubular portion comprises a concave bottom.

According to another embodiment, the hemispherical or spherical surface of the second end of the elongated body of the pin is adjacent to the concave bottom of the recess of the second tubular portion.

According to another embodiment, the elongated body of the pin comprises a retaining portion; and wherein the second part comprises a retainer engaged with the retaining portion of the pin.

According to another embodiment, the retaining portion is a recess and the retainer is a ledge extending radially inwardly toward the retaining portion of the pin from an edge of the recess.

According to another embodiment, the first tubular portion comprises a portion dimensioned to receive at least a part of the second part; and the second part is at least partially received within the portion of the first tubular portion.

According to another embodiment, the activation assisting assembly comprises a biasing member arranged between a first surface of the first tubular portion and a second surface of the second tubular portion; and wherein the first surface is longitudinally facing towards the second surface.

According to another embodiment, the second tubular portion is axially movable from a first position towards the first tubular portion to the second position; wherein first end of the elongated body of the pin is spaced apart from the cavity of the first tubular portion when the second tubular portion is in the first position, and the first end of the elongated body of the pin is received within the cavity of first tubular portion when the second tubular portion is in the second position.

According to another embodiment, the recess is located at a central portion of the second tubular portion.

According to another embodiment, the cavity is located at a central portion of the first tubular portion.

According to another embodiment, the gravity portion is located in the second end of the elongated body of the pin.

According to another embodiment, the activation assisting assembly is used with a medicament delivery device; the medicament delivery device comprises a housing for accommodating a medicament container, the housing extending along the longitudinal axis between a front end and a back end.

According to another embodiment, the medicament delivery device that comprises the activation assisting assembly, further comprises a trigger button for triggering an operation of the medicament delivery device; wherein the trigger button is movably attached to the back end of the housing; the trigger button is axially movable relative to the housing along the longitudinal axis; and the first part of the activation assisting assembly is fixed to the trigger button and the second part of the activation assisting assembly is fixed to the housing.

According to another embodiment, the medicament delivery device that comprises the activation assisting assembly, further comprises a medicament delivery member cover for surrounding a medicament delivery member connected to the medicament container, the medicament delivery member cover is movably attached to the proximal end of the housing; the delivery member cover is attached to the front end of the housing; the medicament delivery member cover is axially movable relative to the housing along the longitudinal axis; and the first part of the activation assisting assembly is fixed to the housing and the second part of the activation assisting assembly is fixed to the medicament delivery member cover.

According to another embodiment, the medicament delivery device that comprises the activation assisting assembly can be an auto-injector, a manual pen injector, an inhaler or a medical sprayer.

Generally, all terms used in the claims are to be interpreted according to their ordinary meaning in the technical field, unless explicitly defined otherwise herein. All references to "a/an/the element, apparatus, component, means, etc." are to be interpreted openly as referring to at least one instance of the element, apparatus, component, means, etc., unless explicitly stated otherwise.

BRIEF DESCRIPTION OF THE DRAWINGS

Embodiments of the present concept will now be described, by way of example only, with reference to the accompanying drawings, in which:

FIG. 1 schematically shows an exploded view of an activation assisting assembly.

FIG. 2A schematically shows a perspective view of a first part of the activation assisting assembly of FIG. 1.

FIG. 2B schematically shows a perspective view of a second part of the activation assisting assembly of FIG. 1.

FIG. 5A schematically shows a perspective view of a first part of the activation assisting assembly of FIG. 4.

FIG. 5B schematically shows a perspective view of a second part of the activation assisting assembly of FIG. 4.

FIG. 5C schematically shows a cross-section view of the second part of the activation assisting assembly of FIG. 4.

FIG. 6 schematically shows a cross-section view of the activation assisting assembly of FIG. 4.

DETAILED DESCRIPTION

Figure 3:
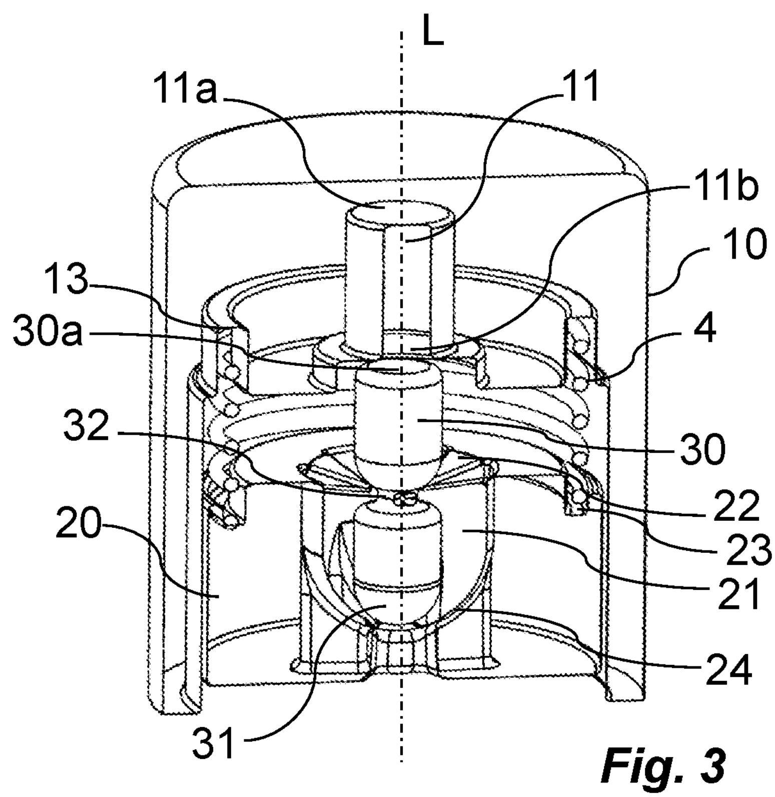
FIG. 3 schematically shows a perspective cross-section view of the activation assisting assembly of FIG. 1.

The activation assisting assembly comprises a first part 1; 1' and a second part 2; 2'. The first part 1; 1' and the second part 2; 2' can be formed in any suitable shape, dependent on the design of a medicament delivery device, especially the design of the activation mechanism of the medicament delivery device. For example, if the activation mechanism of the medicament delivery device comprises a housing and a trigger button, the first part 1; 1' and the second part 2; 2' may be formed according to the shapes of the trigger button and the housing. For example, if the medicament delivery device comprises a cylindrical trigger button or a rectangular trigger button, the first part 1; 1' may also be formed as a cylindrical element or a rectangular element. In another example, the first part 1; 1' may comprise a cylindrical portion or rectangular portion to be attached to the activation mechanism of the medicament delivery device.

The first part 1; 1' comprises a first tubular portion 10; 10' extending along a longitudinal axis L. The second part 2; 2' comprises a second tubular portion 20; 20'. The activation assisting assembly comprises a pin 3; 3' and, optionally, a biasing member 4, as shown in FIG. 1, FIG. 3, FIG. 4 and FIG. 6.

Figure 4:
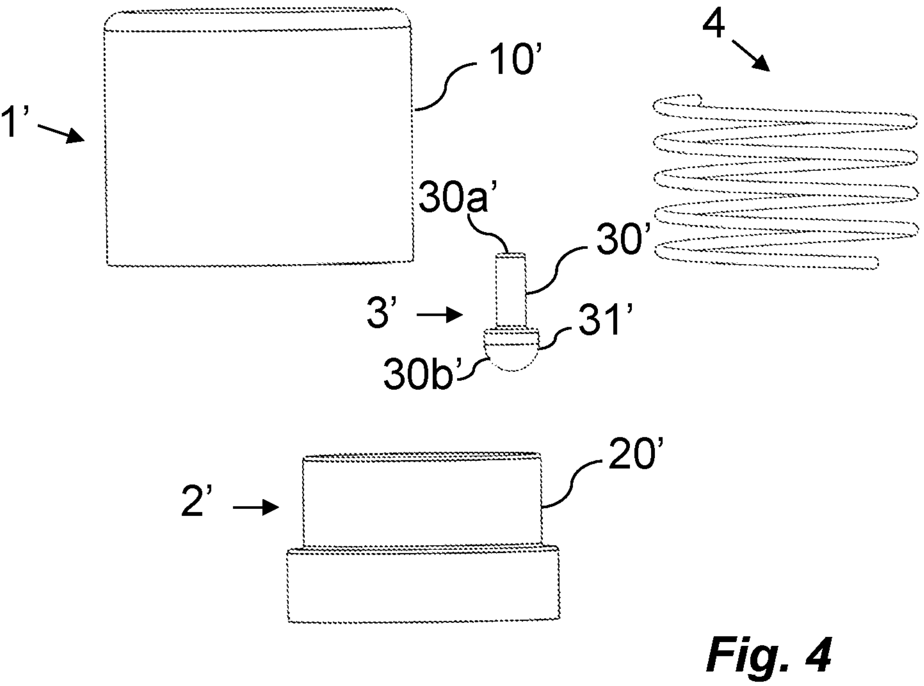
FIG. 4 schematically shows an exploded view of another embodiment of an activation assisting assembly.
Figure 7A:
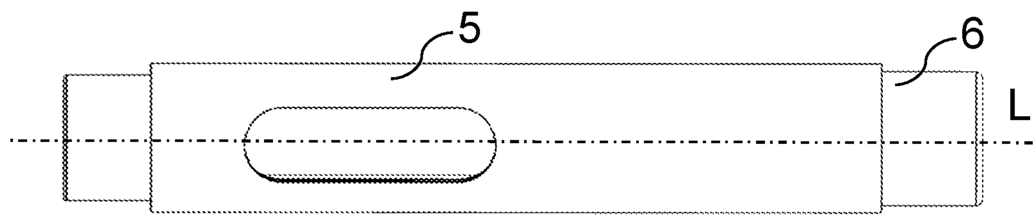
FIGS. 7A-7B schematically show a side and a cross-section view of a medicament delivery device with the activation assisting assembly of FIG. 1.
Figure 7B:
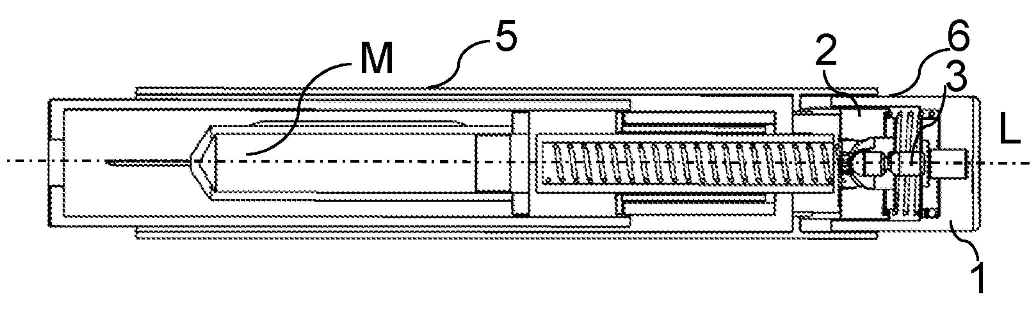
Figure 8A:
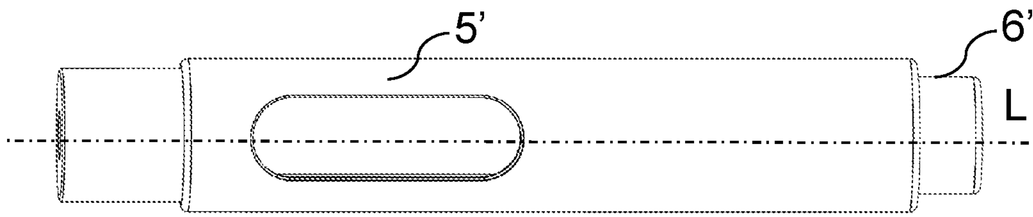
FIGS. 8A-8B schematically show a side and a cross-section view of a medicament delivery device with the activation assisting assembly of FIG. 4.
Figure 8B:
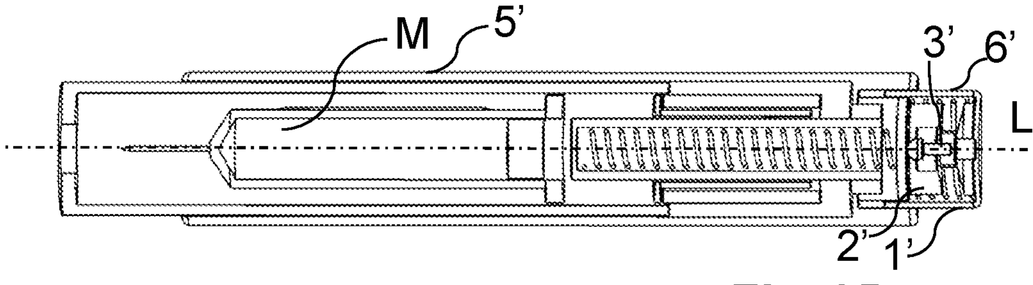

As shown in FIG. 1 and FIG. 4, the pin 3; 3' comprises an elongated body 30; 30' extending between a first end 30*a*; 30*a'* and a second end 30*b*; 30*b'*. The pin 3; 3' comprises a gravity portion 31; 31' where a center of gravity of the pin 3; 3' is located. The gravity portion 31; 31' is located closer to the second end 30*b*; 30*b'* of the elongated body 30; 30' of the pin 3; 3' than to the first end 30*a*; 30*a'* of the elongated body 30; 30' of the pin 3; 3'. Namely, the elongated body 30; 30' of the pin 3; 3' may be evenly divided into two portions with same longitudinal length by a virtual middle line transverse to the longitudinal axis. The gravity portion 31; 31' of the pin 3; 3' can be located in any position between the virtual middle line and the second end 30*b*; 30*b'*. With this structure, the first end 30*a*; 30*a'* of the elongated body 30; 30' of the pin 3; 3' will therefore be vertical relative to the ground due the location of the center of gravity of the pin 3; 3'. The second end 30*b*; 30' of the elongated body 30; 30' of the pin 3; 3' comprises a hemispherical or spherical surface in the described examples, although the concept would still work with other shapes. In some examples, the gravity portion 31; 31' of the pin 3; 3' comprises a material different with a material that the rest of the elongated body 30; 30' of the pin 3; 3' is made from, for example, the elongated body 30; 30' of the pin 3; 3' can be made from plastic, and the gravity portion 31; 31' of the pin 3; 3' may further comprises metal material; alternatively or additionally, a density of the material of the gravity portion 31; 31' of the pin 3; 3' is different from a density of the material that the rest of the elongated body 30; 30' of the pin 3; 3' is made from.

Further, in some embodiments, the pin 3 may comprise a retaining portion 32, as shown in FIG. 1 and FIG. 3.

The first tubular portion 10; 10' comprises a cavity 11; 11' extending along the longitudinal axis L between a first end 11*a*; 11*a'* and a second end 11*b*; 11*b'*. The second end 11*b*; 11*b'* of the cavity 11; 11' comprises an opening. The first end 30*a*; 30*a'* of the elongated body 30; 30' of the pin 3; 3' is dimensioned to fit into the cavity 11; 11'; namely, a dimension of the cavity 11; 11' is slightly greater than a dimension of the first end 30*a*; 30*a'* of the elongated body 30; 30' of the pin 3; 3'; and in a preferred embodiment, a shape of the cavity 11; 11' should be similar to a shape of the first end 30*a*; 30*a'*, so that the cavity 11; 11' can snugly encircle the first end 30*a*; 30*a'* of the elongated body 30; 30' of the pin 3; 3' only when the first end 30*a*; 30*a'* of the elongated body 30; 30' of the pin 3; 3' is aligned with the opening of the cavity 11; 11'.

In one example, the first tubular portion 10; 10' may comprise a portion 12; 12' dimensioned to receive at least a part of the second part 2; 2'. In a preferred example, the portion 12; 12' of the first tubular portion 10; 10' is dimensioned to receive at least a part of the second tubular portion 20; 20' of the second part 2; 2', so that the at least a part of the second tubular portion 20; 20' of the second part 2; 2' is telescopically connected with the first tubular portion 10; 10' of the first part 1; 1'.

Further, if the activation assisting assembly comprises a biasing member 4, the first tubular portion 10; 10' may also comprise a first surface 13; 13' configured to be adjacent to one end of the biasing member 4, as shown in FIGS. 2A and 5A. In one example, the first surface 13; 13' can be a rim of the first tubular portion 10; 10'. The second tubular portion 20; 20' comprises a recess 21; 21'; and if the activation assisting assembly comprises the biasing member 4, the second tubular portion 20; 20' may also comprise a second surface 23; 23' configured to be adjacent to the other end of the biasing member 4, as shown in FIG. 2B and FIG. 5B. In one example, the second surface 23; 23' can be a rim of the second tubular portion 20; 20'. In one embodiment, the second part 2 comprises a retainer 22, as shown in FIG. 2B.

The biasing member 4 is an optional component for the activation assisting assembly. The biasing member 4 allows the first part 1; 1' to move relative to the second part 2; 2' after an injection has been completed. For example, if the activation assisting assembly is attached to a medicament delivery device between a housing of the medicament delivery device and a medicament delivery member cover (and medicament delivery member cover needs to extend relative to the housing after injection), then the activation assisting assembly should comprise the biasing member 4. On the other hand, the activation assisting assembly doesn't need to comprise a biasing member. One example of this is if the activation assisting assembly is attached to a disposable medicament delivery device between a housing of the medicament delivery device and a trigger button that is configured to be pressed one time for triggering the medicament delivery operation.

Further, in another example, the recess 21; 21' of the second tubular portion 20; 20' may comprise a concave bottom 24; 22', as shown in FIG. 3 and FIG. 5C; so that if the second end 30*b*; 30*b'* of the elongated body 30; 30' of the pin 3; 3' comprises a hemispherical or spherical portion, the concave bottom 24; 22' may be a compact shape for receiving the second end 30*b*; 30*b'* of the elongated body 30; 30' of the pin 3; 3', which can minimize space usage within a completed medicament delivery device.

When the activation assisting assembly has been assembled, as shown in FIG. 3 and FIG. 6, the second tubular portion 20; 20' is axially aligned with the first tubular portion 10; 10'. The second tubular portion 20; 20' is axially movable relative to the first tubular portion 10; 10'. The second tubular portion 20; 20' is configured to be moved towards the first tubular portion 10; 10' from a first position to a second position. The opening of the cavity 11; 11' of the first tubular portion 10; 10' directs towards the recess 21; 21' of the second tubular portion 20; 20'. The pin 3; 3' is movably connected to the second tubular portion 20; 20', and is axially arranged between the cavity 11; 11' of the first tubular portion 10; 10' and the recess 21; 21' of the second tubular portion 20; 20'. The first end 30*a*; 30*a'* of the elongated body 30; 30' of the pin 3; 3' is distal to the recess 21; 21', and the second end 30*b*; 30*b'* of the elongated body 30; 30' of the pin 3; 3' is proximal to the recess 21; 21' of the second tubular portion 20; 20'.

The cavity 11; 11' and/or the recess 21; 21' can be arranged at a central portion of the activation assisting assembly. For example, the cavity 11; 11' can be arranged at a central portion of the tubular portion 10; 10' of the first part 1; 1'; and the recess 21; 21' can be arranged at a central portion of the second tubular portion 20; 20' of the second part 2; 2'; as the example shown in FIG. 3 and FIG. 6. However, the position of the cavity 11; 11' and/or the recess 21; 21' relative to the activation assisting assembly can be dependent on the design of the shape of the pin, or the design of what orientation that the medicament delivery device should be held during an operation of the medicament delivery device, or the design of providing a tactile indication to the user during manipulation of the activation mechanism.

The second end 30*b*; 30*b'* of the elongated body 30; 30' of the pin 3; 3' is arranged within the recess 21; 21' of the second tubular portion 20; 20'. In one example, the pin 3 is connected to the second tubular portion 20 through the retaining portion 32 of the pin 3 and the retainer 22 of the second tubular portion 20. The retaining portion 32 is located between the first end 30*a* of the elongated body 30 and the second end 30*b* of the elongated body 30; the exact location of the retaining portion 32 may be dependent on the design of an activation mechanism of a medicament delivery device with the activation assisting assembly. For example, if a trigger button of a medicament delivery device is designed to be pressed with a longer distance for activating an operation of the medicament delivery device, the retaining portion 32 of the pin 3 may located closer to the second end 30*b* of the elongated body 30 than the first end 30*a* of the elongated body 30. Alternatively, if the trigger button of a medicament delivery device is designed to be pressed with a shorter distance for activating an operation of the medicament delivery device, the retaining portion 32 of the pin 3 may be located closer to the first end 30*a* of the elongated body 30 than the second end 30*b* of the elongated body 30.

In a preferred example, the gravity portion 31 of the pin 3 is located between the second end 30*b* of the elongated body 30 of the pin 3 and the retaining portion 32 of the pin 3.

The retaining portion 32 can be an annular recess around the elongated body 30 of the pin 3 as shown in FIG. 3. The retainer 22 can be one or more ledges extending radially inwardly towards the retaining portion 32 of the pin 3 from an edge of the recess 21, so that the pin 3 can only pivot relative to an engagement between the ledge of the second tubular portion 20 and the retaining portion 32 of the pin 3. Alternatively, the retaining portion can be a recess or multiple discrete recesses on and/or around the elongated body 30 of the pin 3; or the retaining portion may comprise a flange or one or more protrusions for engaging with the retainer of the second tubular portion 20. The retainer of the second tubular portion 20 may be a recess, particularly in cases where the retaining portion of the pin 3 comprises a flange or one or more protrusions.

The hemispherical or spherical surface of the second end 30*b'* of the elongated body 30' of the pin 3' can be adjacent to the concave bottom 22' of the recess 21' of the second tubular portion 20', as shown in FIG. 6. In this example, the first tubular portion 10' comprises a support surface 14' facing towards the second tubular portion 20'. The cavity 11', in this example, extends through the support surface 14' along the longitudinal axis L, and the opening of the cavity 11' is located on a central portion of the support surface 14'. The second tubular portion 20' comprises a counter support surface 24' facing towards the support surface 14' of the first tubular portion 10'. The recess 21', in this example, is located at the central portion of the counter support surface 24'. The recess 21' extends through the counter support surface 24' along the longitudinal axis L. Preferably, a longitudinal distance between the support surface 14' of the first tubular portion 10' and the counter support surface 24' of the second tubular portion 20' should be less than a height of the pin 3' measured along the longitudinal axis L. The movement of the pin 3' is therefore limited by the support surface 14' and the counter support surface 24'. In a preferred embodiment, the counter support surface 24' inclines radially outward relative to the longitudinal axis L from the edge of the recess 21', so that even in embodiments where the pin 3' could escape from the recess 21', the hemispherical or spherical part of the second end 30*b*; 30*b'* of the elongated body 30; 30' of the pin 3' can easily slide back into the concave bottom 22' of the recess 21' along the counter support surface 24'; similarly, the support surface 14' can also be inclining radially outward relative to the longitudinal axis L from the edge of the opening of the cavity 11'.

The pin 3; 3' is movable relative to the first tubular portion 10; 10' and the second tubular portion 20; 20'. The pin 3; 3' is configured to be moved relative to the first tubular portion 10; 10' and the second tubular portion 20; 20' by a movement of the gravity portion 31; 31' of the pin 3; 3'. For example, the pin 3; 3' may move radially relative to the first tubular portion 10; 10' and the second tubular portion 20; 20' when the activation assisting assembly is shaken.

The center of gravity of the pin 3; 3' is located in the gravity portion 31; 31' of the pin 3; 3', and the gravity portion 31; 31' of the pin 3; 3' is located closer to the second end 30 *b*; 30 *b'* of the elongated body 30; 30' than the first end 30 *a*; 30 *a'* of the elongated body 30; 30'. As a result, the second end 30 *b*; 30 *b'* of the elongated body 30; 30' will always point to the ground if it can within the confines of the structure of the activation assisting assembly. When the activation assisting assembly is held with the longitudinal axis L being generally perpendicular to the ground (e.g. the longitudinal axis L is 90+/−10 degrees relative to the ground), the pin 3; 3' will also try to align along the longitudinal axis L, because the second end 30 *b*; 30 *b'* of the elongated body 30; 30' of the pin 3; 3' is trying to point to the ground along the longitudinal axis L. When the activation assisting assembly is held with the longitudinal axis L being not generally perpendicular to the ground, for example, the activation assisting assembly may be held with the longitudinal axis L having a tilting angle of 45 degrees with the ground; in this case, the second end 30 *b*; 30 *b'* of the elongated body 30; 30' of the pin 3; 3' will still try to point to the ground and therefore try to move the pin 3; 3' relative to the first tubular portion 10; 10' and the second tubular portion 20; 20' with a tilting angle of 45 degrees with the ground, which stops the pin from entering the cavity.

In one example, the activation assisting assembly is designed to assist the user to always hold the medicament delivery device vertically relative to the ground. The cavity 11; 11' of the first tubular portion 10; 10' extends along the longitudinal axis L and is dimensioned to snugly encircle the first end 30*a*; 30*a'* of the elongated body 30; 30' of the pin 3; 3', so that, the first end 30*a*; 30*a'* can only be axially aligned with the opening of the cavity 11; 11' of the first tubular portion 10; 10' when the pin 3; 3' is aligned along the longitudinal axis L.

FIG. 3 and FIG. 6 show the second tubular portion 20; 20' in the first position relative to the first tubular portion 10; 10'. When the second tubular portion 20; 20' is in the first position, the first end 30*a*; 30*a'* of the elongated body 30; 30' of the pin 3; 3' is spaced apart from the cavity 11; 11' of the first tubular portion 10; 10'. When the activation assisting assembly is held with the longitudinal axis L being generally perpendicular to the ground, meaning that the activation assisting assembly is held vertically relative to the ground, the pin 3; 3' is therefore aligned along the longitudinal axis L; so that the first end 30*a*; 30*a'* is also axially aligned with the opening of the cavity 11; 11' of the first tubular portion 10; 10'. If the second tubular portion 20; 20' is moved, from the first position to the second position, the pin 3; 3' will also be moved towards the cavity 11; 11' of the first tubular portion 10; 10', so that the first end 30*a*; 30*a'* of the elongated body 30, 30' of the pin 3; 3' moved through the opening of the cavity 11; 11' and therefore the first end 30*a*; 30*a'* of the elongated body 30; 30' is received within the cavity 11; 11' of the first tubular portion 10; 10' when the second tubular portion 20; 20' is in the second position.

On the other hand, if the activation assisting assembly is held with the longitudinal axis L being not generally perpendicular to the ground (i.e. the activation assisting assembly is not held vertically to the ground), the pin 3, 3' will be angled relative to the longitudinal axis L; so that the first end 30*a*, 30*a'* of the elongated body 30, 30' of the pin 3, 3' is misaligned with the cavity 11, 11' of the first tubular portion 10, 10'. The cavity 11, 11' is preferably dimensioned to snugly surround the first end 30*a*, 30*a'* of the elongated body 30, 30' of the pin 3, 3'. As a result, if the pin 3, 3' is tilted relative to the longitudinal axis L when the second tubular portion 20, 20' is moved towards the first tubular portion 10, 10', such movement will be limited by the pin 3, 3', so that the second tubular portion 20, 20' cannot move into the second position.

It should be noted that the axial length of the elongated body 30, 30' of the pin 3, 3' that will be received within the cavity 11, 11' of the first tubular portion 10, 10' is dependent on the design of a medicament delivery device that the activation assisting assembly is connected to. For example, the axial length of the elongated body 30, 30' of the pin 3, 3' that will be received within the cavity 11, 11' of the first tubular portion 10, 10' is dependent on how deep a trigger button of a medicament delivery device should be pressed for triggering an operation of the medicament delivery device.

FIGS. 7A-7B and FIGS. 8A-8B show an example medicament delivery device comprises the activation assisting assemblies of FIGS. 1 and 4 respectively. In this example medicament delivery device, the medicament delivery device comprises a housing 5, 5' for accommodating a medicament container. The housing 5, 5' extends along the longitudinal axis L between a front end and a back end. The medicament delivery device comprises a trigger button 6, 6' axially movable relative to the housing between a non-pressed position and a pressed position. The trigger button 6, 6' is for triggering an operation of the medicament delivery device when the trigger button 6, 6' moves into the pressed position. The trigger button 6, 6' is attached to the back end of the housing 5, 5'.

The first part 1, 1' of the activation assisting assembly is fixed to the trigger button 6, 6' and the second part 2, 2' of the activation assisting assembly is fixed to the housing 5, 5'. The first position of the second tubular portion 20, 20' relative to the first tubular portion 10, 10' corresponds to the non-pressed position of the trigger button 6, 6' relative to the housing 5, 5'. The second position of the second tubular portion 20, 20' relative to the first tubular portion 10, 10' corresponds to the pressed position of the trigger button 6, 6' relative to the housing 5, 5'.

In an example where the activation assisting assembly is configured to assist the user to hold the medicament delivery device vertically to the ground, as mentioned above, if the activation assisting assembly and the medicament delivery device are not held vertically to the ground, the second tubular portion 20, 20' cannot move into the second position (corresponds to the pressed position of the trigger button 6, 6' in this example), since such movement will be blocked by the tilting pin 3, 3'. The trigger button 6, 6' therefore cannot move into the pressed position if the medicament delivery device is not held vertically relative to the ground.

In another example, instead of using a trigger button to trigger an operation of the medicament delivery device, an operation of the medicament delivery device can be triggered by an axial movement of a medicament delivery member cover. In this example, the medicament delivery device comprises a medicament delivery member cover axially movable relative to the front end of the housing of the medicament delivery device. The medicament delivery member cover is configured to cover a medicament delivery member connected to the medicament container within the housing of the medicament delivery device. The medicament delivery device is axially movable relative to the front end of the housing between an extended position where the medicament delivery member is covered by the medicament delivery member cover and a retracted position where the medicament delivery member is not covered by the medicament delivery member cover. An operation of the medicament delivery device can be designed to be triggered when the medicament delivery member cover moves into the retracted position.

In this example, the first part of the activation assisting assembly is fixed to the housing and the second part of the activation assisting assembly is fixed to the medicament delivery member cover. The first position of the second tubular portion relative to the first tubular portion is configured to correspond to the extended position of the medicament delivery member cover relative to the housing in this example. The second position of the second tubular portion relative to the first tubular portion is configured to correspond to the retracted position of the medicament delivery member cover relative to the housing in this example.

As mentioned above, if the activation assisting assembly and the medicament delivery device is not held vertically to the ground, the second tubular portion cannot move into the second position (corresponds to the retracted position of the medicament delivery member cover in this example), since such movement will be blocked by the tilting pin. The medicament delivery member cover therefore cannot move into the retracted position if the medicament delivery device is not held vertically relative to the ground.

FIGS. 1-8B illustrate example activation assisting assemblies for a medicament delivery device. In general, these activation assisting assemblies can be configured to assist a user for always holding the medicament delivery device with a predetermined orientation relative to the ground during an operation of the medicament delivery device. For example, the activation assisting assembly may assist the user in always holding the medicament delivery device vertically to the ground when the user performs a medicament delivery operation or a priming operation. The activation assisting assembly can be configured to connect to an activation mechanism of the medicament delivery device, namely the mechanism that is able to trigger an operation of the medicament delivery device, e.g. a medicament delivery operation or a priming operation. For example, the activation mechanism can be a mechanism for releasing a plunger rod of the medicament delivery device from being held against a spring or gas force; or a mechanism for switching on a motor, to actuate a plunger rod of the medicament delivery device.

The activation assisting assembly can be configured to connect to an activation mechanism of a medicament delivery device. The activation assisting assembly can be designed so that the activation mechanism is only able to be activated when the medicament delivery device is held with a predetermined orientation relative to the ground.

The present concept has mainly been described above with reference to a few examples. However, as is readily appreciated by a person skilled in the art, other embodiments than the ones disclosed above are equally possible within the scope of the present concept, as defined by the appended claims.

The invention claimed is:

1. An activation assisting assembly for a medicament delivery device, the activation assisting assembly comprising:

- a first part having a first tubular portion extending along a longitudinal axis (L); wherein the first tubular portion comprises a cavity extending along the longitudinal axis (L) between a first end and a second end; wherein the second end of the cavity comprises an opening;
- a second part having a second tubular portion axially aligned with the first tubular portion, and being axially movable relative to the first tubular portion; wherein the second tubular portion comprises a recess facing towards the opening of the cavity of the first tubular portion;
- a pin movably connected to the second tubular portion; wherein the pin comprises an elongated body extending between a first end, distal from the recess of the second tubular portion, and a second end, proximal to the recess of the second tubular portion;
- wherein the first end of the elongated body of the pin is dimensioned to fit into the cavity;
- wherein the pin comprises a gravity portion where a center of gravity of the pin is located;
- wherein the gravity portion is located in the second end of the elongated body of the pin;
- wherein the second end of the elongated body of the pin is arranged within the recess of the second tubular portion.

2. The activation assisting assembly for the medicament delivery device as claimed in claim 1, wherein the second end of the elongated body of the pin-comprises a hemispherical or spherical surface.

3. The activation assisting assembly for the medicament delivery device as claimed in claim 1, wherein the gravity portion of the pin comprises a material different from a material that the rest of the elongated body of the pin is made from.

4. The activation assisting assembly for the medicament delivery device as claimed in claim 3, wherein a density of the material of the gravity portion of the elongated body of the pin is different from a density of the material that the rest of the elongated body of the pin is made from.

5. The activation assisting assembly for the medicament delivery device as claimed in claim 1, wherein the recess of the second tubular portion comprises a concave bottom.

6. The activation assisting assembly for the medicament delivery device as claimed in claim 5, wherein a hemispherical or spherical surface of the second end of the elongated body of the pin is adjacent to the concave bottom of the recess of the second tubular portion.

7. The activation assisting assembly for the medicament delivery device as claimed in claim 1, wherein the elongated body of the pin comprises a retaining portion; and wherein the second part comprises a retainer engaged with the retaining portion of the pin.

8. The activation assisting assembly for the medicament delivery device as claimed in claim 7, wherein the retaining portion is a recess and the retainer is a ledge extending radially inwardly toward the retaining portion of the pin from an edge of the recess.

9. The activation assisting assembly for the medicament delivery device as claimed in claim 1, wherein the first tubular portion comprises a portion dimensioned to receive at least a part of the second part; and wherein the second part is at least partially received within the portion of the first tubular portion.

10. The activation assisting assembly for the medicament delivery device as claimed in claim 1, wherein the activation assisting assembly comprises a biasing member arranged between a first surface of the first tubular portion and a second surface of the second tubular portion; and wherein the first surface is longitudinally facing towards the second surface.

11. The activation assisting assembly for the medicament delivery device as claimed in claim 1, wherein the recess is located at a central portion of the second tubular portion.

12. The activation assisting assembly for the medicament delivery device as claimed in claim 1, wherein the cavity is located in a central portion of the first tubular portion.

13. A medicament delivery device comprising the activation assisting assembly as claimed in claim 1; wherein the medicament delivery device comprises

- a housing for accommodating a medicament container, the housing extending along the longitudinal axis (L) between a front end and a back end; and
- a trigger button for triggering an operation of the medicament delivery device; wherein the trigger button is movably attached to the back end of the housing;
- wherein the trigger button is axially movable relative to the housing along the longitudinal axis (L); and
- wherein the first part of the activation assisting assembly is fixed to the trigger button and the second part of the activation assisting assembly is fixed to the housing.

14. A medicament delivery device comprising the activation assisting assembly as claimed in claim 1; wherein the medicament delivery device comprises

- a housing for accommodating a medicament container, the housing extending along the longitudinal axis (L) between a front end and a back end; and
- a medicament delivery member cover for surrounding a medicament delivery member connected to the medicament container, wherein the medicament delivery member cover is movably attached to the proximal end of the housing; wherein the delivery member cover is attached to the front end of the housing;

wherein the medicament delivery member cover is axially movable relative to the housing along the longitudinal axis; and wherein the first part of the activation assisting assembly is fixed to the housing and the second part of the activation assisting assembly is fixed to the medicament delivery member cover.

15. An activation assisting assembly for a medicament delivery device, where the activation assisting assembly comprises:

a first part having a first tubular portion extending along a longitudinal axis (L), where the first tubular portion comprises a cavity extending along the longitudinal axis (L) between a first end and a second end and where the second end comprises an opening;

a second part having a second tubular portion axially aligned with the first tubular portion and being axially movable relative to the first tubular portion, where the second tubular portion comprises a recess facing towards the opening of the cavity of the first tubular portion; and a pin movably connected to the second tubular portion, where the pin comprises an elongated body having a first density and extending between a first end that is distal from the recess of the second tubular portion and a second end that is proximal to the recess of the second tubular portion, where the second end comprises a hemispherical or spherical surface, wherein the first end of the elongated body of the pin is dimensioned to fit into the cavity, wherein the pin comprises a gravity portion located where a center of gravity of the pin is located and having a second density that is greater than the first density, wherein the gravity portion is located closer to the second end of the elongated body of the pin than to the first end of the elongated body of the pin, and wherein the second end of the elongated body of the pin is arranged within the recess of the second tubular portion.

16. The activation assisting assembly of claim 15, wherein the hemispherical or spherical surface of the second end is adjacent to a concave bottom of the recess of the second tubular portion.

17. The activation assisting assembly of claim 15, wherein the elongated body further comprises a retaining portion configured as a recess, where a retainer in the second part comprises a ledge extending radially inwardly toward the retaining portion from an edge of the recess.

18. The activation assisting assembly of claim 15 further comprising a biasing member positioned between the first tubular portion the second tubular portion.

19. The activation assisting assembly of claim 15, wherein the cavity is located in a central portion of the first tubular portion and axially aligned with the first end of the elongated body.

* * * * *